United States Patent [19]

Pfisterer et al.

[11] Patent Number: 4,910,996
[45] Date of Patent: Mar. 27, 1990

[54] GAS CHROMATOGRAPH MODIFICATION

[75] Inventors: Egbert A. Pfisterer, Willowdale; Cezary L. Krynicki; Walter T. Hogg, both of Mississauga, all of Canada

[73] Assignee: The Molson Companies Limited, Ontario, Canada

[21] Appl. No.: 185,694

[22] Filed: Apr. 26, 1988

[30] Foreign Application Priority Data

May 14, 1987 [CA] Canada .................................. 537187

[51] Int. Cl.⁴ ............................................. G01N 31/08
[52] U.S. Cl. ...................................... 73/23.1; 422/89; 73/19
[58] Field of Search ..................... 73/19, 23.1; 422/89; 436/161; 55/7, 67, 386

[56] References Cited

U.S. PATENT DOCUMENTS

| | | | |
|---|---|---|---|
| 2,920,478 | 1/1960 | Golay | 73/23.1 |
| 3,511,080 | 5/1970 | Roof | 73/23.1 |
| 3,896,659 | 7/1975 | Goodman | 73/23.1 |
| 4,003,257 | 1/1977 | Flecher et al. | 73/23.1 |
| 4,067,226 | 1/1978 | Ririe | 73/23.1 |
| 4,236,404 | 12/1980 | Ketchum et al. | 73/19 |
| 4,257,259 | 3/1981 | Ford | 73/61.1 C |
| 4,359,891 | 11/1982 | Ahlstrom, Jr. et al. | 73/23.1 |
| 4,704,141 | 11/1987 | Frebber | 73/23.1 |

Primary Examiner—Hezron E. Williams
Attorney, Agent, or Firm—Anthony J. Casella; Gerald E. Hespos

[57] ABSTRACT

An apparatus to measure the concentration of a constituent of a solution containing dissolved gas includes a conduit connectable to a source of the solution. Flow controllers are provided on the conduit, selectively to permit the flow of the solution in the conduit. Pressure regulators are also provided on the conduit to control the pressure of the solution in the conduit, and maintain the pressure in the conduit means at a level sufficiently high to prevent gassification of dissolved gas in the solution, thereby to prevent foaming in the conduit. A gas chromatographic analyser (GCA) is in communication with the conduit via a sampling valve, to permit the flow of discrete samples of solution into the GCA for analysis. The interior of the GCA is maintainable at the same pressure as in the conduit.

12 Claims, 1 Drawing Sheet

4,910,996

GAS CHROMATOGRAPH MODIFICATION

BACKGROUND OF THE INVENTION

The present invention relates to the field of brewing.

More particularly, the present invention relates to a method and apparatus for the quantitative analysis of alcohol and carbon dioxide in beer.

Currently, to test beer for alcohol (i.e. ethanol) content or any other component than $CO_2$, it must first be de-gassed (i.e. the $CO_2$ must be removed). This is because conventional laboratory techniques including gas chromatographic analyses are based on the exact measurement of a defined sample quantity (volume or weight); partially de-gassed or carbonated beer samples cannot be measured accurately because of the inherent instability of the sample specimen and as a consequence inaccurate analytical results are obtained. The upshot of the foregoing is, it is currently impossible to determine alcohol content in beer accurately with an in-line process gas chromatographic analyzer (GCA). Hence, de-gassification of discrete samples is done prior to alcoholic content determination by a GCA.

Unfortunately, however, when beer is de-gassified prior to analysis, it is inevitable that some ethanol is lost. This further complicates the problem of alcohol determination as the discrete sample which has been de-gassed will no longer be representative of the batch from which it originated.

A further problem associated with the use of a process GCA for ethanol determination is that solids (mainly carbohydrates and proteins) from the beer tend to accumulate in the GCA, necessitating its frequent dis-assembly for cleaning.

The object of the present invention is to provide an apparatus by which the alcohol concentration in a pressurized beer sample may be gauged without de-gassing the beer. A further object of the present invention is the design of an apparatus for use in the in-line chromatographic analysis of alcohol in beer which provides the required CIP (cleaning-in-place) for continuous operation.

SUMMARY OF THE INVENTION

In one broad aspect, the present invention relates to an apparatus to measure the concentration of a constituent of a solution containing dissolved gas including: (a) conduit means connectable to a source of said solution; (b) flow control means on said conduit means, selectively to permit the flow of said solution in said conduit means; (c) pressure regulation means on said conduit means to control the pressure of said solution in said conduit means, and maintain the pressure in said conduit means at a level sufficiently high to prevent gassification of said dissolved gas in said solution, thereby to prevent foaming in said conduit means; (d) a gas chromatographic analyser (GCA) in communication with said conduit means via a sampling valve, to permit the flow of discrete samples of said solution into said GCA for analysis, the interior of said GCA being maintainable at the same pressure as in said conduit means.

In another broad aspect, the present invention relates to a method of measuring the concentration of a constituent in a solution containing a dissolved gas, including the steps of: (a) introducing a quantity of said solution into a pressurizable conduit; (b) pressurizing said solution in said conduit, to prevent gassification of the dissolved gas in the solution; (c) providing a gas chromatographic analyser (GCA) in communication with said conduit via a liquid sampling valve, and maintaining a pressure in said GCA equal to that in said conduit; (d) measuring the desired constituent concentration in said solution with said GCA.

BRIEF DESCRIPTION OF THE DRAWINGS

In drawings which illustrate the present invention by way of example.

DETAILED DESCRIPTION OF THE PREFERRED EMBODIMENTS

Figure 1:
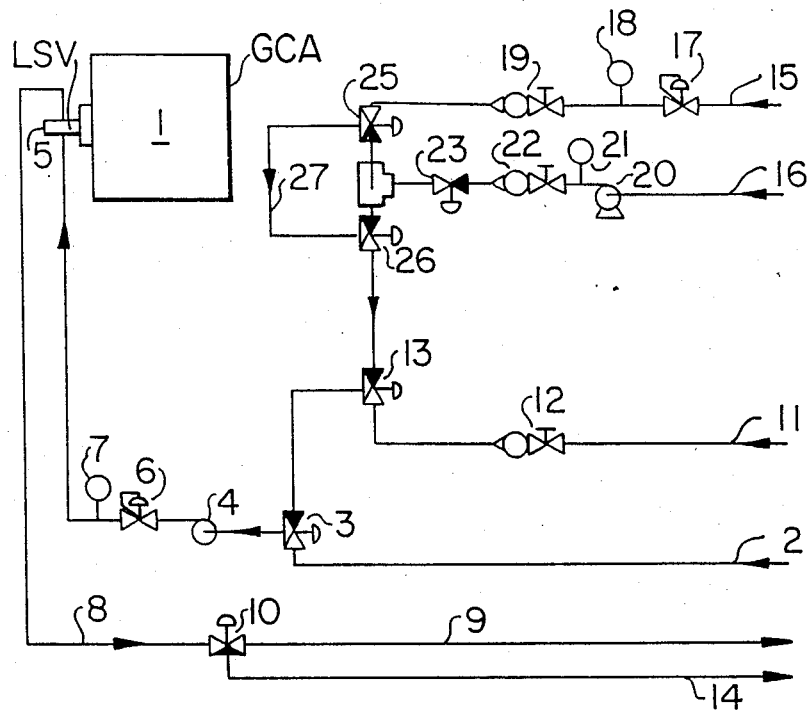
FIG. 1 is a schematic of an embodiment of the present invention adapted to in-line determination of alcohol content in beer.

Referring first to FIG. 1, the present invention provides a sampling system which may be used to analyse the alcohol content of beer directly from the production lines in a brewery. An analyser 1 is connected to the production line in a brewery via a process beer supply line 2. The beer in the line 2 is, of course, carbonated and at sub-ambient temperatures—both of which conditions had previously to be altered before analysis, and neither of which is altered utilizing the present invention. The beer flows through an air actuated valve 3 and is drawn into the sampling area with the aid of pump 4.

The beer flows from the pump 4 to a liquid sampling valve 5, where a quantity can be diverted to a gas chromatographic analyser 1, which is any suitable standard process GCA unit. Between the line 2 and the analyser 1, a pressure of 80 psia is maintained in the analyser by a pressure regulator 6 on the main sample line. Pressure is monitored with a pressure indicator 7 on this line. The pressure in the sample line is necessary to deliver a uniformly liquid sample to the analyser. Maintenance of this pressure prevents the undesired separation of carbon dioxide from the liquid which otherwise would result in foam in the sample line. The size of the injected beer sample is predetermined and relatively small (0.5 microliter) and foam in the sample line would lead to inaccurate measurements.

The major part of the beer flowing through the sampling line will not be diverted to the analyser, but will be returned via return line 8 and will pass through air actuated drain/process return valve 10 to process return line 9, which flows to the main production line in the brewery.

It has been found, using the system outlined above, that by maintaining back pressure in the sampling line and similar pressure in the GCA, a sample with a $CO_2$ content can be analysed, with no fluctuation upon vaporization in the GCA to cause unreproducable results.

To calibrate the GCA 1 used in the present invention, a calibration standard (having a known concentration of the thing to be analysed) is taken in through line 11, past flow indicator 12 and through air actuated valves 13 and 3 to the sampling area described above, where a sample of the known standard is analysed to calibrate the analyser 1. Of course, a series of known standards must be analysed before calibration of the analyser is complete. Also, it will be noted that valve 10 will be open to drain line, rather than process return line 9 during calibration.

The system of the present invention also has a clean-in-place (CIP) sub-system built into it. Lines 15 and 16 respectively feed hot water and cleaning solvent into the CIP sub-system, from whence it can be allowed to flow into the main sampling system. A pressure regulator 17 and pressure indicator 18 are provided on the hot water line, to ensure that the pressure in this line is kept at acceptable levels (as will be a matter of choice to one skilled in the brewing art and especially in plant maintenance). Also, a flow indicator is provided on the hot water line so that a suitable quantity of hot water may easily be mixed with the solvent solution in-put through line 16.

Carefully measured quantities of cleaning solution are drawn through line 16 by metering pump 20 and pass through pressure indicator 21, flow indicator 22 and valve (air actuated) 23 to mixing coil 24. At the same time as when cleaning solution is let into coil 24, air actuated valve 25 on the hot water line is opened to allow hot water into the coil 24 and after the water and solution are mixed, air actuated valve 26 is opened and valves 13 and 3 are opened to permit a flow of mixed water and cleaning solution to pass through the sampling area and clean any deposited solids therefrom.

Valve 10 should, of course, be set to drain line 14 to permit used solution to be disposed of. After the sampling system has been cleaned with cleaning solution, it is flushed with hot water by opening valve 25 to by-pass line 27 (to by-pass coils 24), closing valve 23 and opening valves 26, 13, 3 and 10 to permit hot water flow through the sampling area and out the drain.

Figure 2:
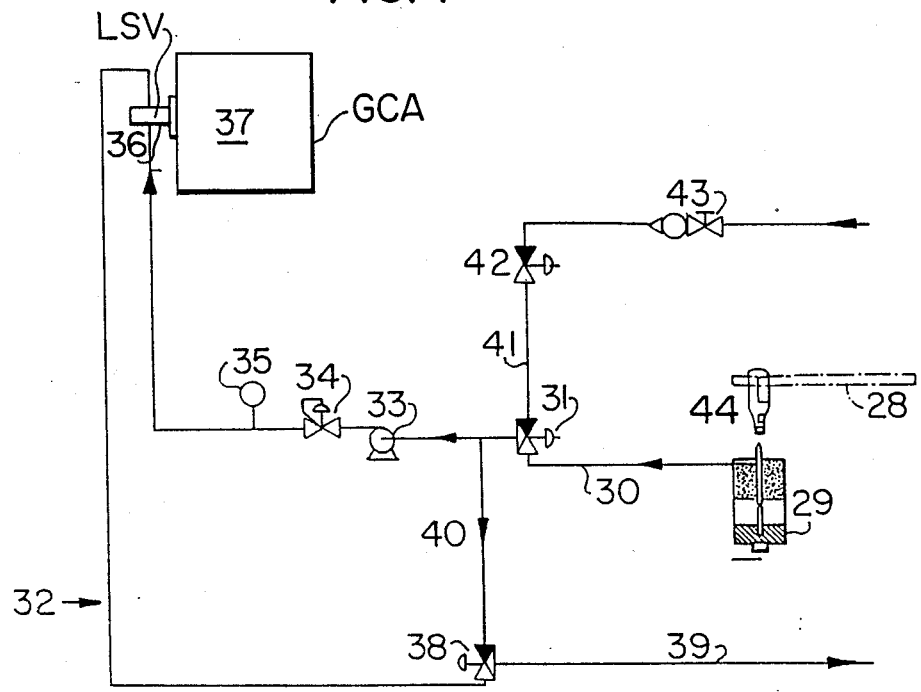
FIG. 2 is a schematic of an embodiment of the present invention adapted for laboratory analysis of the alcohol content of discrete samples of beer.

The system of pressurized gas chromatography of the present invention may also be used in laboratory analysis of discrete samples (bottles or cans) of finished product beer, for quality control as illustrated schematically in FIG. 2.

A container 44, either a bottle or can of beer is placed in holder 28 which holds it securely while a sampling mechanism 29 is pneumatically driven into the container 44 to draw out the contents thereof. These contents flow through sampling line 30 through sampling valve 31 into the sampling loop 32 and through sampling pump 33 used to develop 80 PSI in the sampling loop 32. The loop further includes a pressure regulator 34 and pressure indicator 35, for accurate regulation and monitoring of the pressure in the loop 32.

A liquid sampling valve 36 on the loop 32 is used to divert samples to GCA 37, the column of which is kept pressurized 80 PSI.

Completing the sampling loop is loop drain valve 38 which may be opened to drain line 39 when analysis is complete or to loop return line 40 for the actual sampling procedure. When fluid is injected into the loop from sampling mechanism 29, it fills the loop, at which time valve 38 is closed to drain line 39 and opened to loop return line 40. Simultaneously, valve 31 is closed, which completes the loop, and permits pressurization thereof. To analyse the next sample, valve 38 is opened to drain line 39 and the sample in the loop discharged; the cycle is then repeated The laboratory system illustrated in FIG. 2 also includes a cleaning sub-system, much modified from the full in-line CIP system disclosed above. The cleaning sub-system of the FIG. 2 apparatus is merely a line 41 provided with a valve 42 and a flow indicator 43, into which line, and thence into the loop, may be injected cleaning solution, hot rinse water or calibration standard solution.

It is to be understood that the examples described above are not meant to limit the scope of the present invention. It is expected that numerous variants will be obvious to the person skilled in the brewing art, without any departure from the spirit of the present invention. Moreover, the use of the present invention for use in measuring other constituents of beer, such as $CO_2$, will be evident to the skilled practitioner in the brewing arts. The appended claims, properly construed, form the only limitation upon the scope of the present invention.

We claim:

1. An apparatus to measure the concentration of ethanol in carbonated beer containing dissolved gas including:
   (a) conduit means connectable to a brewery production line to permit a flow of said carbonated beer therethrough;
   (b) flow control means on said conduit means, selectively to permit the flow of said solution in said conduit means;
   (c) pressure regulation means comprising a pump connected to said conduit means to maintain a back pressure in said conduit means at a level sufficiently high to prevent gassification of said dissolved gas in said carbonated beer, thereby to prevent foaming in said conduit means and a pressure regulator with an associated pressure indicator for maintaining the pressure in said conduit means at a constant desired level;
   (d) a gas chromatographic analyser (GCA) in communication with said conduit means via a sampling valve, to permit the flow of discrete samples of said carbonated beer into said GCA for analysis of the ethanol content thereof, the interior of said GCA being maintainable at the same pressure as in said conduit means.

2. An apparatus as described in claim 1, wherein said flow control means comprise valves on said conduit means selectively to permit a flow of beer from said brewery production line to said GCA and selectively back to said production line or to a drain line.

3. An apparatus as described in claim 1, wherein the pressure regulation means in said conduit means is capable of maintaining a constant pressure in said conduit means at between 60 and 100 psia.

4. An apparatus as described in claim 3, wherein the pressure regulation means in said conduit means is capable of maintaining a constant pressure in said conduit means at between 70 and 90 psia.

5. An apparatus as described in claim 3, wherein the pressure regulation means in said conduit means is capable of maintaining a constant pressure in said conduit means at 80 psia.

6. An apparatus as described in claim 3, further including a calibration line connected to said conduit means for delivering a flow of a standard solution of known analytical value, for instance ethanol concentration, to said GCA for calibration thereof.

7. An apparatus as described in claim 3, further including a cleaning subsystem connected to said conduit means for the cleansing thereof, said subsystem including:
   (i) a pipeline connectable to a hot water supply;
   (ii) a pipeline connectable to a source of cleansing solvent;
   (iii) a mixing coil in which said hot water and solvent can intermingle;

(iv) a pipeline leading from said mixing coil to said conduit means, for the cleaning thereof; and (v) a by-pass pipe for permitting a flow of hot water past said coil and to said conduit means, for the rinsing thereof.

8. An apparatus to measure the concentration of a constituent of carbonated beer containing dissolved gas including:

(a) conduit means for receiving and delivering the contents of a discrete container of the beer to a loop of pipeline;

(b) flow control means on said loop for selectively permitting the flow of said solution in said loop;

(c) pressure regulation means comprising a pump on said loop for controlling the pressure of said beer in said loop, and maintaining the pressure in said loop at a level sufficiently high to prevent gassification of said dissolved high to prevent gassification of said dissolved gas in said solution, thereby to prevent foaming in said conduit means and a pressure regulator provided with a pressure indicator for maintaining the pressure in the loop at a constant desired level; and (d) a gas chromatographic analyser (GCA) in communication with said loop via a sampling valve, to permit the flow of discrete samples of said beer into said GCA for analysis, the interior of said GCA being maintainable at the same pressure as in said loop.

9. An apparatus as described in claim 8, wherein said pressure regulation means is capable of maintaining a constant pressure of between 60 and 100 psia.

10. An apparatus as described in claim 8, wherein said pressure regulation means is capable of maintaining a constant pressure of between 70 and 90 psia.

11. An apparatus as described in claim 8, wherein said pressure regulation means is capable of maintaining a constant pressure at 80 psia.

12. An apparatus as described in claim 9, including a further pipeline leading into said loop and connected thereto by a valve, for permitting the flow of cleansing solution, rinse water of GCA calibration standard to said loop.

* * * * *